United States Patent [19]
Fuchs et al.

[11] Patent Number: 5,221,871
[45] Date of Patent: Jun. 22, 1993

[54] SURFACE WAVE GAS SENSOR

[75] Inventors: Harald Fuchs, Carlsberg; Wolfgang Schrepp, Heidelberg; Michael Rapp, Sindelfingen; Siegfried Hunklinger, Heidelberg; Manfred von Schickfus, Neckargemuend, all of Fed. Rep. of Germany

[73] Assignee: BASF Aktiengesellschaft, Ludwigshafen, Fed. Rep. of Germany

[21] Appl. No.: 764,697

[22] Filed: Sep. 24, 1991

[30] Foreign Application Priority Data

Sep. 28, 1990 [DE] Fed. Rep. of Germany ....... 4030651

[51] Int. Cl.$^5$ .............................................. H01L 41/08
[52] U.S. Cl. ................................ 310/313 R; 73/24.01
[58] Field of Search .............................. 310/313, 312; 73/DIG. 4, 24.01, 204.11, 204.14, 204.17

[56] References Cited

U.S. PATENT DOCUMENTS

| | | | |
|---|---|---|---|
| 4,243,960 | 1/1981 | White et al. | 310/313 R X |
| 4,312,228 | 1/1982 | Wohitjen | 310/313 R X |
| 4,547,648 | 10/1985 | Longway | 310/366 X |
| 4,726,225 | 2/1988 | Brace et al. | 310/313 R X |
| 4,932,255 | 6/1990 | Brace et al. | 310/313 R X |
| 5,051,645 | 9/1991 | Brace et al. | 310/313 D |
| 5,076,094 | 12/1991 | Frye et al. | 310/313 R X |

OTHER PUBLICATIONS

Wohitjen, Sensors and Actuators, 5 (1984) 307-324.
Sensors and Actuators, 10 (1986) 47-64, Venema et al.

*Primary Examiner*—Mark O. Budd
*Attorney, Agent, or Firm*—Keil & Weinkauf

[57] ABSTRACT

A high-sensitivity surface wave gas sensor in which the interaction of a surface wave field with a solid film suitable for adsorbing the gas to be determined causes a change in the frequency of an oscillating circuit containing a surface wave delay line as a function of the type and concentration of the gas entails the delay line provided for adsorption of the gas being completely coated with the solid film, and the dimensions of the delay lines being such that the length of the surface wave transformer is greater than that of the delay line.

16 Claims, 3 Drawing Sheets

SURFACE WAVE GAS SENSOR

The present invention relates to a high-sensitivity surface wave gas sensor in which the interaction of a surface wave field with a solid film suitable for adsorbing the gas to be determined causes a change in the frequency of an oscillating circuit containing a surface wave delay line as a function of the type and concentration of the gas.

The detection and the quantitative determination of gaseous emissions are becoming increasingly important. In order to be able to carry out such measurements quickly, accurately and even at very low concentration of the substance to be determined, without complex apparatus, surface wave gas sensors are increasingly being developed. These entail surface waves, called Rayleigh waves, being generated on a piezoelectric material. These surface waves must, on their path from the emitter to the receiver, pass through a thin film which is capable of reversible adsorption of the gas to be determined. The resulting change in mass alters the velocity of propagation of the surface wave along the coated part of its propagation pathway. The resulting alteration in phase of the surface wave generates in the resonance circuit a change, which is approximately proportional thereto, in the resonance frequency, which provides a measure of the interaction with the gas to be determined. The mass sensitivity of a surface wave gas sensor is expressed by an alteration in the resonance frequency which is proportional to the square of the resonance frequency and to the change in the mass deposited on the adsorbing surface (Wohltjen, Sensors and Actuators, 5 (1984) 307-324). The sensitivity of a surface wave gas sensor is thus proportional to the square of its resonance frequency. The mode of action of the film then determines which gas is detected or the extent to which detection is specific for a particular gaseous substance.

An early description of a sensor based on an oscillating circuit with a surface wave delay line is given in U.S. Pat. No. 4,312,228. According to this, based on the previously known effect, surface waves are used to determine, for example, the thickness of vacuum vapor-deposited layers, and the piezoelectric material which is the path for the surface wave is coated with a layer which is selective for a substance and then the properties of the surface wave are determined. In order to provide a gas sensor on this basis, it is necessary for the layer covering the delay line to interact selectively, either by physisorption or by chemisorption, with the gas to be determined (Wohltjen, Sensors and Actuators. 5 (1984) 307-324). Substances specified as suitable for this are phthalocyanine complexes with various central atoms such as Pb, Cu, Fe and others, and metal-free complexes with hydrogen as central substituent, which are suitable for detecting $NO_2$, $Cl_2$, $NH_3$, $F_2$ and other molecules with high electron acceptor capacity.

However, the hitherto disclosed gas sensors have frequently experienced problems with arbitrary mode discontinuities, and poor drift stability of the resonance frequency because of a great temperature variation of the surface wave propagation velocity when, as is usual, lithium niobate is used as substrate material. This temperature variation has an adverse effect on the frequency stability despite a compensatory reference circuit. It is not possible to increase the sensitivity sufficiently by using smaller frequencies either, without at the same time having to accept longer response times owing to the use of thicker absorption layers. In addition to the pure and rapid adsorption on the surface, thicker films of this type allow adsorption in deeper layers, and although, on the one hand, this increases the sensitivity, on the other hand it increases the response time owing to the slower diffusion connected with the absorption.

It is an object of the present invention to provide a surface wave gas sensor which does not have the above-mentioned disadvantages and which has, in particular, a high sensitivity for extremely low gas concentrations and a short response time.

We have found that this object is achieved by a gas sensor which is essentially composed of a surface wave delay line which determines the frequency of an oscillating circuit, where a less than 0.1 μm thick organic, non-conducting solid film is located on the delay line to adsorb the gas to be determined, wherein the delay line is completely coated with the solid film, the delay line has a resonance frequency in the range from 0.5 to 2 GHz and has dimensions such that the surface wave transformer length is greater than the length of the delay line and the transformers are designed so that the response curve in the response spectrum of the delay line does not permit mode discontinuities, corresponding to a small band width.

The number of delay lines is preferably two. In an embodiment of the novel gas sensor with more than two delay lines, the other delay lines can be coated with solid films which have either a different thickness of the adsorbing material layer for extending the sensitivity range or else different solid films for determining different gases.

BRIEF DESCRIPTION OF THE DRAWINGS

In order to facilitate an even greater understanding of the present invention, attention is now directed to the drawings.

Figure 1:
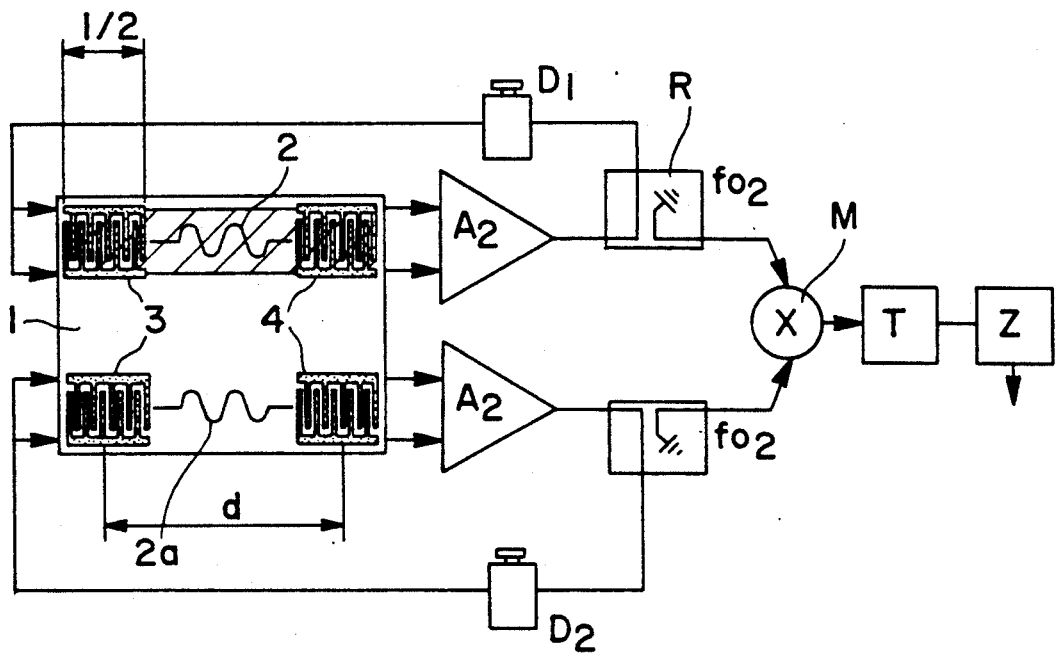
FIG. 1 is an electrical schematic diagram in conjunction with associated electrical devices depicting an embodiment of the surface wave gas sensor of the present invention.

The novel gas sensor is depicted diagrammatically in FIG. 1. Two separate delay lines 2 and 2a are applied to a piezoelectric substrate 1, and one of them is coated with the solid film adsorbing the gas to be determined. The transformers (3 and 4) which are at each end of the delay lines, the emitter and receiver of the surface waves are composed of what are called paired fingers which are vapor-deposited on the piezoelectric substrate. As an example, the transformer may be composed of about 1900 paired fingers to generate a surface wave on the substrate with a wavelength of 5.25 μm. Each of these surface wave units is part of an HF oscillating circuit composed of an amplifier $A_1$ ($A_2$), of an attenuating element $D_1$ ($D_2$), which can be switched in narrow steps of, for example, 0.1 dB, to attenuate the signal to a loop gain of the entire resonance circuit which is as near 1 as possible. A directional coupler $R_1$ ($R_2$) is used to extract without contact a certain portion, for example $-20$ dB, from the signal going round the resonance circuit. The effect of this is that interference from the evaluation side of the electronics can likewise exert an influence on the resonance circuit only with the corresponding attenuation, which further increases the frequency stability. The signal is then mixed with the parallel oscillating circuit for temperature compensation by means of an HF mixer M, and then the differential frequency $\Delta f$ is filtered out of the mixed signal by means of a low-pass filter T. This signal is counted with a frequency counter Z and thus the differential frequency is determined and evaluated.

Figure 3:
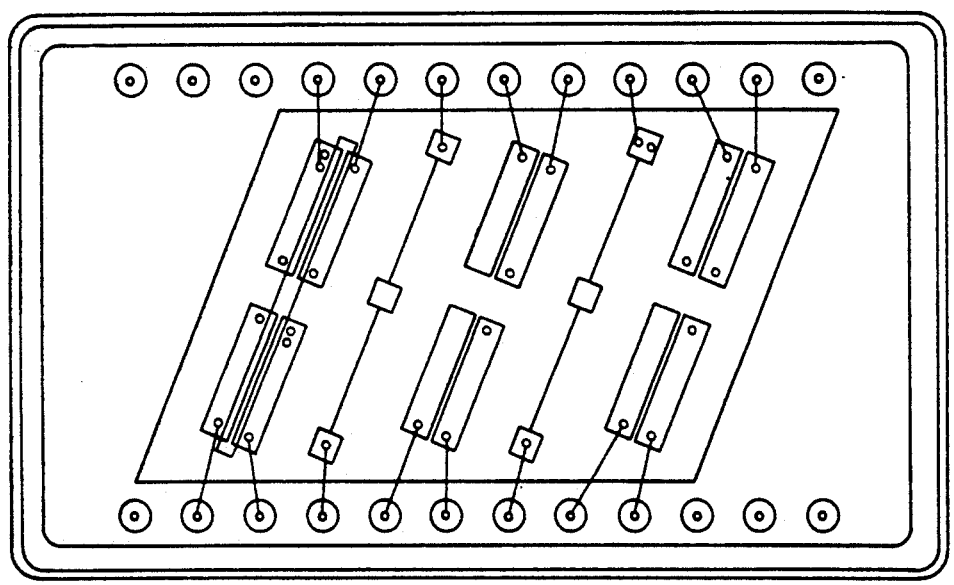
FIG. 3 is a top plan view of a gas sensor that can accurately and precisely measure surface temperature of the substrate and solid film. Particularly depicted are vapor-deposited aluminum strips which act as thermal resistances which measure surface temperature.

To carry out a measurement with the novel gas sensor it is necessary to ensure high temperature stability of the measurement unit. Used for this are aluminum strips which are likewise vapor-deposited on the substrate and which act as thermal resistances and measure the temperature directly on the surface of the substrate. This makes possible accurate temperature control of the substrate and of the solid film. A gas sensor of this type is shown in the Figure (FIG. 3).

In the embodiment of the surface wave gas sensor it is expedient to choose an angle between the direction of propagation of the surface wave and the cut edge of the substrate which differs from 90° and is advantageously 115°, so that the surface waves emerging from the back of the transformer are unable to be reflected back into the transformer. This avoids directly adjacent, interfering transmission lines in the surface wave spectrum of the delay line. It is thus unnecessary to attach an acoustic sink which is normally present on the crystal cut edge of the substrate. Quartz is particularly suitable as substrate material. This material has a very low temperature variation of the surface wave propagation velocity and, moreover, the crystal cut can be chosen so that, when the operating temperature of the solid adsorption film is optimal, the compensation point, i.e. the maximum propagation velocity, is present and thus has a temperature variation of zero at this temperature.

The complete coating of the two delay lines with an ultrathin sensitive solid film as required can be achieved, in particular, as monolayer or multilayer with the Langmuir-Blodgett technique. These coatings can also be produced by vapor deposition or sublimation under reduced pressure. If the gas-selective layer of the substratelayer is coupled by covalent or ionic bonding to the adhesion layer of the substrate, this leads to a high receptor packing density and thus to a high sensitivity of the gas sensor.

The novelty of a gas sensor of this type is that the entire delay line and not just the area between the transformers is coated with the solid film suitable for adsorbing the gas to be determined. Another essential feature of the gas sensor according to the invention is the establishment of the length of the delay line. If a delay line is operated inside a resonance circuit, the number of phase transitions located thereon is arbitrary as long as the relevant wavelength yields with $v_0$ a resonance frequency which is within the band width. The resonance frequency may thus change abruptly, caused by small random disturbances. Such jumps in frequency are called mode discontinuities which, by their nature, cause great interference. This interference can be prevented by selecting a length of delay line d, i.e. e distance between centers of transducers, along a surface path which is smaller than the length of the transducers 1. The length of a tranducer is in this case $\frac{1}{2}$1 (FIG. 1). This now makes interfering mode discontinuities impossible when their frequency separation is greater than the resonance width of the relevant transducer, i.e. d is smaller than 1.

A gas sensor with a design of this type makes it possible to provide a defined output signal without the interfering effect of any mode discontinuity. This results in a strictly reproducible change in the signal during the sorption processes. Moreover, the novel design of the gas sensor means that there is no need to employ an automatic gain control (AGC) as described, inter alia, by Venema et al., Sensors and Actuators, 10 (1986) 47-64. An AGC of this type is intended to suppress the variation in attenuation of the complete delay line taking place during sorption of a gas. However, besides the instrumental complexity, an AGC of this type has the additional disadvantage that the phase in the electrical circuit varies as a function of the electrically controllable amplification. The rapid and automatic adjustment of the loop gain of the oscillating circuit to near 1 which is possible with the AGC is unnecessary in the design of the novel gas sensor because the interfering frequencies generated by the overdriven amplifier are sufficiently attenuated by the efficient filter characteristics of the special delay lines.

There is another reason why an AGC is unnecessary. The variation in attenuation during the adsorption which is normally suppressed by the AGC in the prior art did not occur with the novel sensor because where the coating is confined to the distance between the transformers the oscillating mode is shifted through the stationary response spectrum owing to the phase shift taking place on adsorption. However, where there is complete coating, the oscillating mode is shifted to the same extent as the complete response spectrum on adsorption, so that no additional variation in attenuation is generated because of the lack of relative movement in the frequency range. For the same reason, the novel gas sensor makes it possible for the first time to choose a response spectrum of maximum sharpness with respect to an improved oscillation stability.

The novel gas sensor makes it possible, because of its high sensitivity, to use optimally ultrathin films applied using the sublimation technique (UHV) with thicknesses in the range of a few molecule diameters and, moreover, layers produced by the Langmuir-Blodgett technique. Very short response times can be achieved with these ultrathin films when used in gas sensors because of the restriction to the surface effects produced only by the interaction between the film and the test gas. There can be no effect deriving from slow diffusion into deeper layers of the film in this case, and thus no increase in the response time owing to this. Although it is not possible to use conducting sorption films because the entire delay line is coated with the solid film and thus the transformers would be short-circuited, it is still possible to use organic semiconductors such as phthalocyanine complexes, as ultrathin films for the novel gas sensor because they have a sufficiently high resistance at the film thicknesses used.

As an example, the detection of $NO_2$ using the novel gas sensor is described. For this, the delay line is coated by the Langmuir-Blodgett technique with one or four monolayers of an iron-phthalocyanine complex (Pc complex) of the formula $(C_5H_{11}O)_8FePc$. The sensitivity of the sensor at 40° C. is 5700 Hz/ppm with 4 monolayers and 1900 Hz/ppm with 1 monolayer. This results in an $NO_2$ detection limit of only 1 ppb with a sensor resolution of about 5 Hz for the thicker layer.

Figure 2:
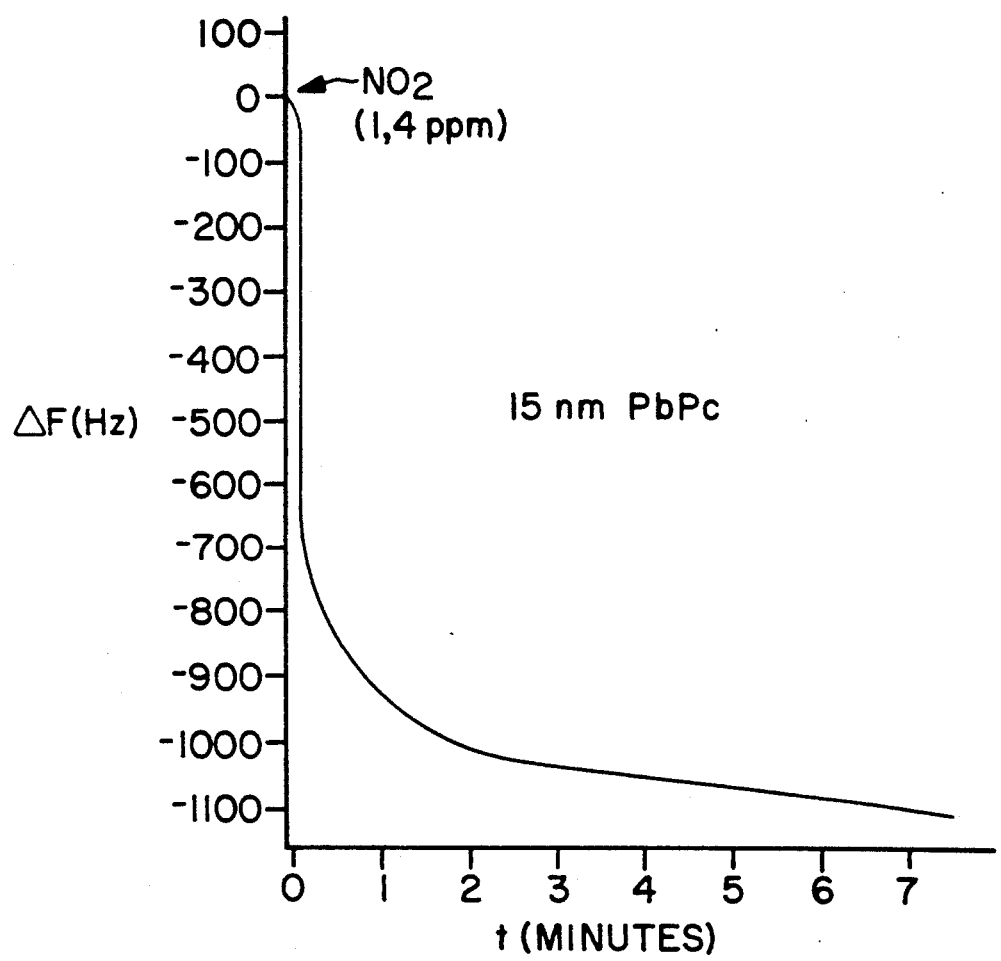
FIG. 2 is a plot of experimental data showing the change in the frequency signal over time when detecting the presence of $NO_2$ at 1,4 ppm by using UHV-sublimed PbPc layers of 15 nm thickness in the surface wave gas sensor of the present invention.

Very good results can also be obtained with UHV-sublimed PbPc layers. The change in the signal is shown in FIG. 2. The layer was sublimed on using a Knudsen cell under UHV at 380° C. The resulting layer was 15 nm thick. The measurement was carried out at 120° C. on an $NO_2$ concentration of 1.4 ppm (in nitrogen). The frequency change ($\Delta f$) occurring with the novel gas sensor within 5 minutes was 1100 Hz. The sensitivity was thus 800 Hz/ppm. Further measurements showed that the sensor response was linearly related to the $NO_2$ concentration. Hence the resolution limit is 6 ppb $NO_2$ in nitrogen.

We claim:

1. A gas sensor which is essentially composed of a surface wave delay line which determines the frequency of an oscillating circuit, where a less than 0.1 μm thick organic, non-conducting solid film is located on the delay line to adsorb the gas to be determined, wherein the delay line is completely coated with the solid film, the delay line has a resonance frequency in the range from 0.5 To 2. GHz includes transformers at each end to define a surface wave transformer length, the delay line has dimensions such that the surface wave transformer length is greater than the length of the delay line and the transformers are designed so that the response curve in the response spectrum of the delay line does not permit mode discontinuities, corresponding to a small band width.

2. The invention of claim 1, wherein an angle between the direction of propagation of the surface wave and a cut edge of a substrate receiving said delay lines differ from 90° to 115°.

3. The invention of claim 2, wherein said substrate comprises quartz and said organic, non-conducting solid film comprises an organic semiconductors.

4. The invention of claim 3, wherein said organic semiconductors comprise phthalocyanine complexes.

5. The invention of claim 1, wherein said coating of organic, non-conducting solid film is defined to be a few molecular diameters.

6. A gas sensor which is essentially composed of a surface wave of at least two delay lines which determine the frequency of an oscillating circuit, where a less than 0.1 μm thick organic, non-conducting solid film is located on the delay lines to adsorb the gas to be determined, wherein the delay lines are completely coated with the solid film, the delay lines having a resonance frequency in the range from 0.5 To 2. GHz and includes transformers at each end to define a surface wave transformer length, the delay lines having dimensions such that the surface wave transformer length is greater than the length of the delay lines and the transformers are designed so that the response curve in the response spectrum of the delay lines do not permit mode discontinuities, corresponding to a small band width.

7. The invention of claim 6, wherein one of said delay lines has said organic, non-conducting solid film of a different thickness than the other delay line.

8. The invention of claim 7, wherein an angle between the direction of propagation of the surface wave and a cut edge of a substrate receiving said delay lines differ from 90° to 115°.

9. The invention of claim 7, wherein said substrate comprises quartz and said organic, non-conducting solid films comprise organic semiconductors.

10. The invention of claim 9, wherein said organic semiconductors comprise phthalocyanine complexes.

11. The invention of claim 6, wherein said coatings of solid films are defined to be a few molecular diameters.

12. The invention of claim 6, wherein one of said delay lines has said organic, non-conducting solid film of a different film than the other delay line.

13. A method of providing a surface wave gas sensor comprising the steps of:

a) providing for a surface wave delay line placed upon a substrate to determine the frequency of an oscillating circuit; said delay line having a resonance frequency in range of from 0.5 to 2. GHz and includes transformer at each end to define a surface wave transformer length, the delay line having dimensions such that the surface wave transformer length is greater than the length of the delay line;

b) completely coating a less than 0.1 μm thick organic nonconducting solid film over said delay line; and c) designing the transformers so that the response curve in the response spectrum of the delay line does not permit mode discontinuities, corresponding to a small band width.

14. The invention of claim 13, additionally including coating said organic, nonconducting solid film by use of Langmuir-Blodgett techniques.

15. The invention of claim 13, wherein the substrate comprises quartz and the organic, non-conducting solid film comprise organic semiconductors.

16. The invention of claim 13, wherein said organic semiconductors comprise phthalocyanine complexes.

* * * * *

UNITED STATES PATENT AND TRADEMARK OFFICE
CERTIFICATE OF CORRECTION

PATENT NO. : 5,221,871

DATED : June 22, 1993

INVENTOR(S) : FUCHS et al.

It is certified that error appears in the above-identified patent and that said Letters Patent is hereby corrected as shown below:

IN THE CLAIMS

Claim 1, line 24, column 5, after "GHz" insert --and--.

Claim 3, line 38, "semiconductors" should read --semiconductor--.

Signed and Sealed this

First Day of March, 1994

Attest:

BRUCE LEHMAN

Attesting Officer  Commissioner of Patents and Trademarks